United States Patent [19]

Sofia

[11] Patent Number: 4,978,680

[45] Date of Patent: Dec. 18, 1990

[54] METHOD FOR THE PREVENTION AND CONTROL OF EPILEPTIC SEIZURE

[75] Inventor: Robert D. Sofia, Willingboro, N.J.

[73] Assignee: Carter-Wallace, Inc., New York, N.Y.

[21] Appl. No.: 412,964

[22] Filed: Sep. 26, 1989

[51] Int. Cl.$^5$ .............................................. A61K 31/24
[52] U.S. Cl. ...................................... 514/534; 514/541
[58] Field of Search ................................ 514/534, 541

[56] References Cited

PUBLICATIONS

Chem-Abst. 104-180056v (1986).

Primary Examiner—Stanley J. Friedman
Attorney, Agent, or Firm—Kevin B. Clarke

[57] ABSTRACT

A novel method for the prevention and control of epileptic seizures employing pharmaceutical compositions containing 2-phenyl-1,3-propanediol dicarbamate.

1 Claim, No Drawings

METHOD FOR THE PREVENTION AND CONTROL OF EPILEPTIC SEIZURE

The present invention relates to pharmaceutical compositions containing 2-phenyl-1,3-propanediol dicarbamate as an active component and to methods for the prevention and control of epileptic seizures by the use of such compositions More particularly, the present invention further relates to methods for increasing epileptic seizure threshold and the prevention of epileptic seizure spread through the administration of therapeutic compositions which contain as an active ingredient 2-phenyl-1,3-propanediol dicarbamate commonly known as Felbamate.

Felbamate is a well known pharmaceutical compound having been described in U.S. Pat. Nos. 2,884,444 and 4,868,327.

Epilepsy, a disease which has been characterized as a paroxysmal, self-sustaining and self-limited cerebral dysrhythmia, genetic or acquired in origin and physiologic or organic in mechanism is generallY divided into four main types based on the type of seizure that occurs in those afflicted with the disease.

Based on clinical and electroencephalographic observations, the four general subdivisions of epilepsy are:
1. Grand mal
2. Petit mal
3. Psychomotor
4. Autonomic Those afflicted with epilepsy may present with any one of or a mixture of the foregoing forms of the disease.

In theory, it is believed that anti-epileptic drugs act to prevent or control seizures by acting on the seizure focus which may be a collection of pathologically altered neurons or normal cells having restricted vascular supply or an injured area in which the neurons of a nerve net have been destroyed.

Up to the present time, all drugs used in the treatment of epilepsy function as prophylactics against the symptoms of epilepsy, i.e., the reduction and control of epileptic seizures as opposed to being curatives.

Although it is generally recognized that approximately 50% of epileptic patients can be controlled with presently available anti-epileptic medications, there is a continuing long felt need for more selective and less toxic anti-epileptic drugs. The desiratum of the art has been to provide a non-toxic, non-sedative, long-acting and highly effective anti-epileptic drugs.

Phenytoin and carbamazepine are presently the drugs of choice for control of both generalized tonic-clonic (grand mal) and complex partial (temporal lobe) epileptic seizures.

In addition to gingival hyperplasia and hirsutism peculiar to phenytoin, both drugs have been reported to induce cerebellar-vestibular effects, skin disorders, hepatic deficiencies and congenital abnormalities. The foregoing toxicity profile for both phenytoin and carbamazepine clearly demonstrates a need for less toxic substances for use as anti-epileptic medications.

One of the objects of the present invention is to provide compositions for the treatment of epilepsy comprising felbamate as the active ingredient.

Another object of the present invention is to provide relatively non-toxic compositions effective to control or prevent epileptic seizures which have a unique spectrum of anti-epileptic activity and which include felbamate as an active component.

A further object of the present invention is to provide compositions for the prevention and control of epileptic seizures which compositions are relatively non-toxic, have a high degree of effectiveness and continue to produce a therapeutic response over relatively long periods of time.

Moreover, it is an object of the present invention to provide methods for the prevention and control of epileptic seizures through the use of felbamate.

Accordingly, it has been found that felbamate chemically described as 2-phenyl-1,3-propanediol dicarbamate is a compound which has demonstrated superior properties when compared to prototype drugs, i.e., phenytoin with respect to increasing seizure threshold and prevention seizure spread.

The compositions for the treatment of epilepsy may take any of a variety of forms although theY are intended primarily for oral use and is suitable for forming into pills, capsules and tablets by well-known practices. When the active ingredient is in the form of a solid, a typical tablet composition comprises 500 milligrams of 2-phenyl-1,3-propanediol dicarbamate intermixed in a dry pulverulent state with suitable solid carriers and diluents.

In general, an effective daily dose of the active ingredient is in the range of from about 100 milligrams to about 5 grams.

Solid carriers and diluents suitable for use include sugars such as lactose and sucrose; cellulose derivatives such as carboxymethyl cellulose, ethyl cellulose, methyl cellulose, etc., gelatin including hard and soft gelatin capsules, talc, cornstarch, stearic acid and magnesium stearate.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets. However, for convenience in manufacturing and ease of administration, it is preferable that each dosage form contains at least 25 milligrams and up to 500 milligrams of 2-phenyl-1,3-propanediol dicarbamate per unit dosage form.

EXAMPLE 1

2-phenyl-1,3-propanediol dicarbamate is constituted into 500 mg. dosage units by encapsulation without an adjuvant into hard gelatin capsules The yield from 1000 g. of 2-phenyl-1,3-propanediol dicarbamate is about 2000 capsules each containing 500 mg. of medicant.

EXAMPLE 2

A tableting formulation is prepared as follows:
83 g. 2-phenyl-1,3-propanediol dicarbamate
13 g. powdered sugar with 3% starch
76 g. corn syrup
q.s. water
13 g. talc U.S.P. powdered Italian
3 g. magnesium stearate
q.s alcohol
flavoring The formulation is compressed into tablets, each containing 200 mg. of 2-phenyl-1,3-propanediol dicarbamate. The yield is about 1750 tablets.

Felbamate (2-phenyl-1,3-propanediol dicarbamate) has a very favorable preclinical profile characterized by a substantial margin of safety (protective index 16.9–19.1). The following example presents the results from a double-blind randomized clinical trial in patients with partial seizures. Criteria for patient entry into the study were 4 or more complex partial seizures per month in spite of treatment with both phenytoin and carbamazepine.

EXAMPLE 3

Fifty-six patients (mean age 31.4 years; male=32, female=24) completed the study. The mean seizure frequencies for the eight week periods analyzed were: baseline=39.8; felbamate=34.9; placebo=40.2. Felbamate was significantly superior to placebo by percent seizure reduction (P=0.018) and truncated percent seizure reduction (p=0.007).

The mean felbamate dose was 2300 mg/day. Plasma felbamate concentrations ranged from 18.4 to 51.9, mean=32.5 mg/ml.

Adverse effects were minor and consisted of nausea and CNS effects.

The superiority of felbamate over placebo in a population of persons with severely refractory epilepsy indicates this medication to be a major anti-epileptic agent.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for reducing the incidence and severity of epileptic seizures which comprises administering to a warm-blooded animal in need of such treatment a therapeutic amount of 2-phenyl-1,3-propanediol dicarbamate.

* * * * *

(12) EX PARTE REEXAMINATION CERTIFICATE (6556th)
United States Patent
Sofia

(10) Number: US 4,978,680 C1
(45) Certificate Issued: Dec. 9, 2008

(54) METHOD FOR THE PREVENTION AND CONTROL OF EPILEPTIC SEIZURE

(75) Inventor: Robert D. Sofia, Willingboro, NJ (US)

(73) Assignee: Medpointe Healthcare Inc., Somerset, NJ (US)

Reexamination Request:
No. 90/007,991, Mar. 30, 2006

Reexamination Certificate for:
Patent No.: 4,978,680
Issued: Dec. 18, 1990
Appl. No.: 07/412,964
Filed: Sep. 26, 1989

(51) Int. Cl.
*A61K 31/21* (2006.01)
*A61K 31/27* (2006.01)
*A61K 31/24* (2006.01)

(52) U.S. Cl. ........................................ 514/534; 514/541
(58) Field of Classification Search .................. None
See application file for complete search history.

(56) References Cited

U.S. PATENT DOCUMENTS 2,724,720 A 11/1955 Berger
2,884,444 A 4/1959 Berger

OTHER PUBLICATIONS

Ewart A. Swinyard et al., "Comparative Anticonvulsant Activity and Neurotoxicity . . . ," 27 Epilepsia 27 (1986) (New York City).

Ewart A. Swinyard et al., "The Effect of Chronic Felbamate Administration . . . ," 29 Epilepsia 295 (1987) (New York City).

A.J. Wilensky et al., Pharmacokinetics of W–544 (ADD 03055) in Epileptic Patients, 26 Epilepsia 602 (1985) (Raven Press, New York).

*Primary Examiner*—Bennett Celsa

(57) ABSTRACT

A novel method for the prevention and control of epileptic seizures employing pharmaceutical compositions containing 2-phenyl-1,3-propanediol dicarbamate.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claim 1 is cancelled.

\* \* \* \* \*